United States Patent [19]

Hess et al.

[11] Patent Number: 4,520,186

[45] Date of Patent: May 28, 1985

[54] POLYURETHANES AND POLYURETHANE-UREAS BASED ON AROMATIC URET DIONE DIAMINE ADDUCTS

[75] Inventors: Heinrich Hess; Gerhard Grögler, both of Leverkusen; Richard Kopp, Cologne, all of Fed. Rep. of Germany

[73] Assignee: Bayer Aktiengesellschaft, Leverkusen, Fed. Rep. of Germany

[21] Appl. No.: 526,245

[22] Filed: Aug. 25, 1983

[30] Foreign Application Priority Data

Sep. 3, 1982 [DE] Fed. Rep. of Germany ....... 3232736

[51] Int. Cl.$^3$ .................. C08G 18/32; C08G 18/77; C07D 1/00
[52] U.S. Cl. ................. 528/73; 260/239 A; 252/182; 528/62; 528/68
[58] Field of Search ............ 260/239 AR; 528/62, 528/73, 68; 252/182

[56] References Cited

U.S. PATENT DOCUMENTS

| | | | |
|---|---|---|---|
| 2,643,250 | 6/1953 | Stallmann et al. | 260/239 |
| 3,475,200 | 10/1969 | Kallert et al. | 117/94 |
| 3,793,238 | 2/1974 | Winkelmann et al. | 260/2.5 AY |
| 3,998,794 | 12/1976 | Müller et al. | 260/77.5 AM |
| 4,176,118 | 11/1979 | Petinaux et al. | 260/239 A |
| 4,251,427 | 2/1981 | Recker et al. | 260/37 N |
| 4,405,752 | 9/1983 | Recker et al. | 524/847 |

FOREIGN PATENT DOCUMENTS 0074023  9/1981  European Pat. Off. ..... 260/239 AR

OTHER PUBLICATIONS

Saunders et al., J.A.C.S., 75 (1953), p. 5439.
Singh et al., Can. J. Chem., 40 (1962), p. 935.

*Primary Examiner*—Herbert S. Cockeram
*Attorney, Agent, or Firm*—Gene Harsh; Joseph C. Gil; Lyndanne M. Whalen

[57] ABSTRACT

Aromatic uret dione diurea diamines corresponding to the formula

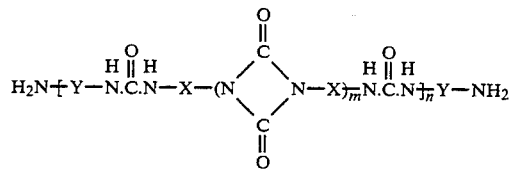

in which X, Y, m and n are as defined herein are produced by reacting an aromatic diamine with a diisocyanate corresponding to a specified formula in a molar ratio of diamine to diisocyanate of at least 1.8 to 1. These diamines are particularly useful in the production of elastomers.

13 Claims, No Drawings

POLYURETHANES AND POLYURETHANE-UREAS BASED ON AROMATIC URET DIONE DIAMINE ADDUCTS

BACKGROUND OF THE INVENTION

This invention relates to aromatic diamines containing uret dione and urea groups corresponding to a specified formula and to a process for the production of such diamines.

Uret dione diamines, i.e. aromatic diamines containing uret dione groups in the same molecule and corresponding to the general formula

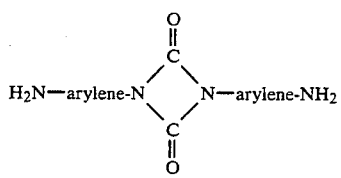

are known to those skilled in the art. Such diamines are useful in incorporating uret dione groups into polyurethanes hardenable by heat (German Offenlegungsschrift No. 2,044,838). They may also be employed in the production of wash-resistant dye finishes on cellulose fibers (U.S. Pat. No. 2,643,250). In such dye finishes, the uret dione diamine is first attached to the cellulose fiber through the uret dione group and the amino groups are then diazotized. The production of aromatic uret dione diamines by the nitration of uret diones, followed by hydrogenation disclosed in U.S. Pat. No. 2,643,250 is, however, extremely complicated.

Aliphatic uret dione diamines are largely unstable. Thus, dimeric tolylene diisocyanate reacts with aliphatic amines even at temperatures below 50° C. and the uret dione ring splits to form urea and biuret groups (JACS 75 (1953) page 5439 and Can. J. Chem. 40 (1962), page 935). This feature of the uret dione group is utilized in the crosslinking of polyurethanes containing uret dione groups by the action of aliphatic diamines (for example, ethylene diamine) to produce crosslinked polyurethane filaments and fibers (German Offenlegungsschrift No. 2,044,838). The less reactive aromatic amines are also capable of splitting the uret dione ring in polyurethanes in solution in dimethyl formamide or dimethyl sulfoxide.

In accordance with German Offenlegungsschriften Nos. 2,941,051, 2,842,805 and 1,570,548, aromatic diamines may be used as chain extenders in addition to dimeric tolylene diisocyanate to produce one-component polyurethane mixtures. However, specific adducts of dimeric tolylene diisocyanate with excesses of diamines are not described in these disclosures.

SUMMARY OF THE INVENTION

It is an object of the present invention to provide new aromatic uret dione diurea diamines.

It is also an object of the present invention to provide a process for the production of aromatic uret dione diurea diamines.

It is a further object of the present invention to produce aromatic uret dione diurea diamines in the form of very fine powders.

It is yet another object of the present invention to provide aromatic uret dione diurea diamines which are stable at temperatures in excess of 100° C.

These and other objects which will be apparent to those skilled in the art are accomplished by reacting a uret dione diisocyanate with an aromatic diamine in a molar ratio of at least 1.8 moles diamine for every 1 mole of diisocyanate to form a uret dione diamine modified by urea groups.

DETAILED DESCRIPTION OF THE INVENTION

It has now been found that aromatic uret dione diurea diamines may be obtained by a simple method in which 1 mole of a uret dione diisocyanate is reacted with approximately 2 moles of an aromatic diamine to form a uret dione diamine modified by urea groups. It is surprising that defined products are formed in this reaction because the uret dione ring could split off and react with the excess diamine to form, for example, the biuret.

The low molecular weight adducts of 1 mole of the aromatic uret dione diisocyanate

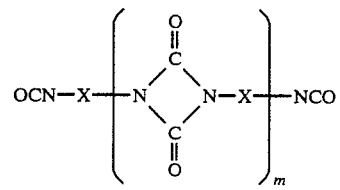

and excess quantities (for example 2 moles) of the aromatic diamine $NH_2$—Y—$NH_2$ are easy to produce. These adducts do not have to be ground after production and drying because they accumulate in the form of very fine powders having a particle size of, for example, from 1 to 3 $\mu$m. These adducts are also stable to splitting of the uret dione ring at temperatures in excess of 100° C.

The aromatic uret dione diurea diamines of the present invention correspond to the formula

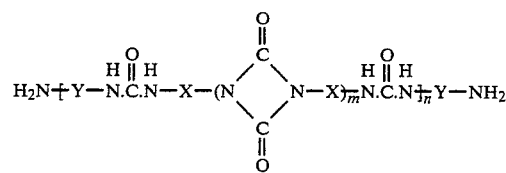

in which
X represents an aromatic radical having a molecular weight of from 76 to 499,
Y represents the same aromatic radical as X or the group

or radicals of a relatively high molecular weight diamine (molecular weight of 500 to 10,000)
where
Z is a radical of the dihydroxy compound HO—Z—OH, n represents the average degree of pre-extension and has
a value of from 1 to 3 (preferably from 1 to 2) and m represents the average degree of uret dionization and has a value of from 1 to 10 (preferably from 1 to 2 and, most preferably, 1), provided that X is not a 2,4'-diphenyl sulfide radical when the diamine H$_2$N—Y—NH$_2$ has a molecular weight greater than or equal to 500.

The present invention also relates to a process for the production of aromatic uret dione diurea diamines corresponding to the formula

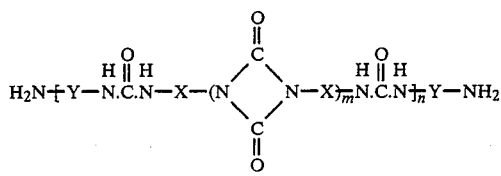

in finely particulate (optionally suspended) form in which a solution or suspension of the aromatic diamine H$_2$N—Y—NH$_2$ is mixed with the uret dione diisocyanate

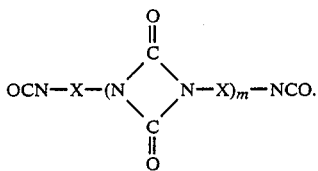

The aromatic diamine may be in solution in an isocyanate-inert solvent, plasticizer or in a relatively high molecular weight polyol. The finely particulate uret dione diisocyanate may be suspended in an isocyanate-inert solvent, plasticizer or in a relatively high molecular weight polyol. The molar ratio of diamine to diisocyanate should generally be such that at least 1.8 moles of diamine (preferably between 1.8 and 2.3) for each mole of diisocyanate are present.

The finely particulate uret dione diurea diamines (optionally suspended in relatively high molecular weight polyhydroxyl compounds) of the present invention are useful as synthesis components in the production of urea-group-containing, high molecular weight polyaddition products (optionally crosslinkable through the uret dione groups). The finely particulate uret dione diurea diamines of the present invention (optionally suspended in relatively high molecular weight polyhydroxyl compounds) may also be reacted with an NCO-prepolymer of a polyol and excess polyisocyanate and/or with polyisocyanates and, optionally, other relatively high molecular weight polyhydroxyl compounds having a molecular weight in the range from 400 to 10,000 and, optionally, low molecular weight chain extending agents (particularly diols or aromatic diamines) having a molecular weight in the range from 62 to 399 at temperatures above 100° C. The equivalent ratio between NCO-groups and the sum of OH- and NH$_2$-groups is generally from 0.9 to 1.4. The product of this reaction may be crosslinked in the presence of excess OH- or NH$_2$-groups at temperatures above 140° C. The products of the reaction of longchain diamines H$_2$N—Y—NH$_2$ having a molecular weight of ≧500 with uret dione diisocyanates (optionally in the presence of other low molecular weight aromatic diamines) at temperatures above 140° C. may be used as a self-crosslinking one-component system.

In the process according to the present invention, a thixotropic, fine suspension is formed and is stirred for several more hours at a temperature ranging from room temperature to 110° C. (preferably from 40° to 50° C.). Since slight "pre-extension" can occur between diisocyanate and diamine, even with a molar ratio of 2:1, a small amount of the excess aromatic diamine generally remains dissolved in the liquid solvent phase. The unreacted diamine may be washed out with organic solvents and the aromatic uret dione diurea diamine filtered off under suction and dried. The IR-spectrum of the product diamines thus-recovered indicates that no free NCO-groups are present. The biuret band is discernible at most, if at all, in the form of a faint shoulder. The uret dione band remains intact, even after the product diamine was heated to 110° C.

The diamine products may of course also be produced by initially introducing the uret dione diisocyanate in solution or suspension to the reaction vessel and then adding the amine.

The uret dione diurea diamines (dimer diamines) of the present invention (optionally suspended in relatively high molecular weight polyhydroxyl compounds) may also be useful as a synthesis component in the production of urea-group-containing, high molecular weight polyurethanes optionally crosslinkable through the uret dione group. The aromatic uret dione diurea diamines are preferably used in solid, finely powdered heterogeneous form for diamine crosslinking by the polyisocyanate polyaddition process. These powder diamines preferably have a particle size in the range from 0.01 to 10 μm (most preferably from 0.1 to 3 μm). The diamine may be made into a paste with or suspended in a polyol and processed together with NCO-prepolymers and/or polyisocyanates and, optionally, other chain extending agents (preferably low molecular weight polyols or aromatic diamines) to form elastomers having surprisingly good properties. Such an elastomer-forming system is stable in storage at room temperature or moderately elevated temperatures. Even at relatively high temperatures, it is free flowing and has a long processing time ("pot life"). Elastomers made with the diamines of the present invention have low compression set coupled with high tensile strength. When heated to 110° C. to complete polyurethane formation, the uret dione ring remains largely intact during heating (as verified by IR-spectra). At heating temperatures in excess of 110° C., the uret dione ring is capable of further reaction accompanied to some extent by further crosslinking of the elastomer.

The problems encountered with heterogeneous diamine crosslinking are generally attributable to the fact that a diamine which is solid and substantially insoluble at room temperature (even when heated to dissolve it) reacts with the free NCO-groups so slowly that a layer of urea is not immediately formed around the solid particles. The aromatic uret dione diurea diamines of the present invention are, however, surprisingly suitable for heterogeneous diamine crosslinking despite their poor solubility.

The aromatic uret dione diurea diamines of the present invention are preferably used as mixtures with relatively high molecular weight compounds containing 2 or more isocyanate-reactive groups (e.g., relatively high molecular weight polyether or polyester polyols or polyether or polyester polyamines) in the form of suspensions or pastes. Such mixtures are generally used instead of the pure uret dione diurea diamines when the mixture of the pure amines with the NCO-prepolymer is no longer readily pourable due to the excessively high ratios by volume between diamine and NCO-prepolymer. Appropriate mixtures may be prepared by working the aromatic uret dione diurea diamines of the present invention into the relatively high molecular weight polyol or polyamine using a high-speed mixer. The diamines of the present invention may also be produced directly in the polyol by dissolving the aromatic diamine (H₂N—γ—NH₂) in the polyol and mixing the resulting solution with the uret dione diisocyanate. The advantage of this single-stage method lies in the fact that no inhomogeneous agglomerates can occur during mixing of the polyurethane components. Mixtures such as these are free-flowing at temperatures of from about 80° to 100° C.

For casting in molds, the mixture of the aromatic uret dione diurea diamine of the present invention and the polyol or polyamine is degassed in vacuo for about 20 to 60 minutes at a temperature from 50° to 100° C. The degassed mixture is then mixed with the prepolymer or molten polyisocyanate (which has optionally been degassed) for about 10 to 30 minutes at 80° to 120° C. The resulting mixture is reacted at a temperature of from 100° to 150° C. (preferably from 110° to 120° C.) and then tempered. Instead of being cast, the mixture may also be injection molded using standard machines, preferably at elevated temperatures in the range from 140° to 200° C.

The equivalent ratio between NCO-groups and the sum of OH- and NH₂-groups in such a mixture may be between 0.9 and 1.4 and preferably between 1.0 and 1.2. In cases where uret dione rings are reacted, the uret dione ring must also be included in the calculation of the NCO-groups present. With sub-equivalent quantities of OH- and NH₂-groups, the elastomer may undergo self-crosslinking through the uret dione groups at sufficiently high temperatures (for example >140° C.).

The aromatic uret dione diurea diamines of the present invention may also be used in admixture with known liquid or readily soluble aromatic di- or polyamines. Polyether polyurethanes produced with mixtures such as these have significantly better mechanical properties than elastomers produced solely with known liquid or readily soluble crosslinking amines (see Examples 28 and 29 infra).

The aromatic uret dione diurea diamines may also behave as self-crosslinking one-component systems if they are heated to temperatures high enough (e.g., in excess of 140° C.) that the uret dione ring reacts with the aromatic NH₂-groups to form biurets. Such one-component systems are preferably produced by reacting a uret dione diisocyanate with a long-chain and a short-chain diamine to obtain elastomers. In cases where the aromatic uret dione diurea diamines have an average degree of uret dionization such that m has a value of greater than 1, more polyol or polyamine may be added to the reaction mixture.

The aromatic uret dione diurea diamines of the present invention having a particularly rigid structure are generally those in which X and Y represent aromatic radicals having molecular weights of from 76 to 499. Specific examples of such radicals are: 1,3- or 1,4-phenylene radicals; 2,4- and/or 2,6-tolylene radicals; 3,5-diethyl-2,4-diamino-tolylene radicals; 3,5-diethyl-2,6-diaminotolylene radicals; 4,4'-diaminodiphenyl methane radicals; diphenyl methane radicals di- and tetra-alkylated in the 3- and/or 5-positions; 4,4'- and/or 2,4'-diphenyl sulfide radicals; 3,3'-dichloro-4,4'-diphenyl methane radicals; 1,5-naphthylene radicals; 3,3'-4,4'-diphenyl radicals; 4,4'-diphenyl sulfone radicals, and other radicals of aromatic diisocyanates or aromatic diamines known by those skilled in the art of polyurethane chemistry. The diamines in which Y is the same as X give especially high-melting, rigid hard segments in polyurethane elastomers.

X preferably represents the 2,4-tolylene radical, the 4,4'-diphenyl methane radical and/or the 2,4'-diphenyl sulfide radical, but most preferably the 2,4-tolylene radical.

If, however, Y represents a radical of a relatively high molecular weight diprimary diamine H₂N—Y—NH₂ having a molecular weight of >500 to 10,000 (preferably from 1000 to 6000) and corresponds to the formula

in which Z represents a radical of dihydroxy compounds HO—Z—OH (e.g., dihydroxy polyether or polyester radicals) the diamines are no longer so extremely high-melting and are elasticized or less rigid (depending upon the length of the radical Z). When such diamines are used to synthesize polyurethanes, less relatively high molecular weight polyol or polyamine is required to elasticize the polyurethane (so-called soft segments). In special cases, the aromatic uret dione diurea diamines may be reacted solely with diisocyanates to form polyurethanes or may even be self-crosslinked at very high temperatures (for example at temperatures above 160° C.) to form polyurethanes.

Y preferably represents 4,4'-diphenyl methane radical; 2,4-tolylene radical; the 3,5-diisopropyl-3',5'-diethyl-4,4'-diphenyl methane radical; the 3,5-diethyl-2,4-(35% 2,6-content)-tolylene radical and/or the 1,4-phenylene radical.

The diamines of the present invention may be used to carry out heterogeneous diamine crosslinking processes (despite their distinctly increased storage stability and poor solubility) to produce high quality elastomers at high temperatures. Elastomers which may be further crosslinked through the uret dione groups already incorporated may also be formed. This further crosslinking may be brought about by increasing the temperature (to 150° C., e.g.) or by the action of highly reactive (aliphatic) polyamines such as ethylene diamine or isophorone diamine to form extremely highly cross-linked systems at the surface.

The aromatic uret dione diurea diamines of the present invention may be used with aromatic diisocyanates such as diphenyl methane-4,4'-diisocyanates for polymer synthesis without any effect upon the stability of the mixtures in storage. The delaying of the reaction (stability in storage) is considerably greater where diamines according to the present invention are used rather than diamines containing electron-attracting substituents (which reduce the basicity of the amino groups) such as 3,3'-dichloro-4,4'-diaminodiphenyl methane or 4-chloro-3,5-diaminobenzoic acid isobutyl ester. The delaying of the reaction is also considerably greater when the diamines of the present invention are used than in cases where complex compounds with salts and amines which decompose only on heating and release the reactive amine (U.S. Pat. No. 3,891,606) are used.

The velocity of the polyaddition reaction may also be controlled by using a diisocyanate, catalyst or crosslinker which dissolves and becomes active only in the presence of heat, as described in specific Examples by H. W. Cox and S. A. Iobst in Plast. Engn. 34 (1978), pages 49 to 52. The use of sparingly soluble diamines which react only in the presence of heat is also known as heterogeneous amine crosslinking and is described in German Offenlegungsschrift No. 2,635,400. In addition to these properties, the diamines of the present invention are extremely rigid in structure and may be self-crosslinking.

Uret dione diisocyanates (dimeric diisocyanates) suitable for the production of the dimer diamines of the present invention include dimeric tolylene-2,4-diisocyanate; dimeric 4,4'-diisocyanatodiphenyl methane and its oligodimeric, linear homologues having up to 4 uret dione rings in the molecule; dimeric 2,4'-diisocyanato-diphenyl sulfide; dimeric 4,4'-diisocyanato-diphenyl sulfide; dimeric 4,4'-diisocyanato-diphenyl sulfone as well as other known aromatic uret dione diisocyanates and mixtures of uret dione diisocyanates. Dimeric tolylene-2,4-diisocyanate and dimeric 2,4'- and/or 4,4'-diisocyanato-diphenyl methane are preferred.

The production of uret dione diisocyanates from the corresponding diisocyanates has been known for some considerable time (cf. Hofmann, Berichte 3 (1870), page 765). The production of dimeric tolylene-2,4-diisocyanate, for example, is described in detail in Kunststoff-handbuch, Vol. 7, Polyurethane, published by Vieweg/Hochtlen, Carl-Hanser-Verlag, Munich, 1966, page 16. Uret dione diisocyanates may be made by dimerization of the above-mentioned diisocyanates with catalysts, such as trialkyl phosphites (German Offenlegungsschrift No. 2,349,726), peralkylated carbamoyl phosphites (U.S. Pat. No. 3,290,288), peralkylated aminophosphines (U.S. Pat. No. 3,290,288), 3- or 4-substituted pyridines such as 4-dimethylaminopyridine (British Pat. Nos. 821,158; 944,309 and 962,689), trialkyl phosphines (air-sensitive highly reactive substance (German Offenlegungsschrift No. 2,420,475)), dialkyl aryl phosphines and alkyl diaryl phosphines (U.S. Pat. No. 2,671,082), trialkyl arsines (Analytical Chemistry of the Polyurethanes, Vol. 16/III, High-Polymers-Series (Wiley 1969), pages 112-131), dibutyl tin dilaurate (German Offenlegungsschrift No. 2,420,475); or in the absence of a catalyst in a carboxylic acid ester (USSR Pat. No. 149,775) or in aqueous emulsion (British Pat. No. 1,134,285).

Oligomeric uret dione diisocyanates corresponding to the following general formula

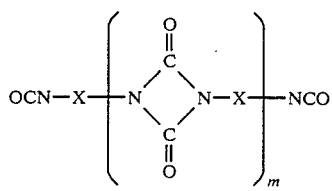

in which X is an aromatic radical and m has a value of from 1 to 10, may also be used. Of these uret dione diisocyanates, it is preferred to use the oligomeric uret dione diisocyanate of 4,4'-diphenyl methane diisocyanate which may be produced at low temperatures (for example 20° C.) in substantially apolar solvents (such as aliphatic hydrocarbons) by the addition of catalysts.

Suitable aromatic diamines $NH_2—Y—NH_2$ for producing the diamines of the present invention include: 3,5-diethyl-2,4-diaminotoluene; 3,5-diethyl-2,6-diaminotoluene and isomer mixtures thereof; 2,4-diaminotoluene and/or 2,6-diaminotoluene; 4,4'- and/or 2,4'-diaminodiphenyl methane; ($C_1$–$C_4$-alkyl)-diaminodiphenyl methanes dialkylated in the 3- and/or 5-position or tetraalkylated in the 3,3',5,5'-positions; p-phenylene diamine; m-phenylene diamine; 4,4'- and 2,4'-diaminodiphenyl sulfide; 3,3'-dimethyl thio-4,4'-diaminodiphenyl methane or naphthylene diamine. In addition to these diamines in which Y represents an aromatic radical having molecular weights of from 76 to 499, Y may also represent residues having molecular weights above 500 to 10,000, preferably in the range from 1000 to 6000. Relatively high molecular weight aromatic di- and polyamines such as those described above may readily be obtained by hydrolyzing NCO-prepolymers of relatively high molecular weight diols, (for example relatively high molecular weight polyether diols or polyester diols) and excess quantities of aromatic diisocyanates (preferably tolylene diisocyanates), soluble or insoluble basic compounds (for example alkali hydroxides, low molecular weight sodium silicates, alkali carbonates or basic ion exchangers) in excess water and in the presence of water-soluble solvents. One such process is described in German Offenlegungsschriften No. 2,948,419 and 3,039,600.

Inert solvents which may be used in the practice of the present invention include aliphatic and aromatic hydrocarbons, ethers, esters and ketones. Specific examples of such solvents are relatively high boiling petroleum ethers, toluene, dioxane, ethyl acetate, methyl ethyl ketone. Plasticizers, such as phthalic acid and isophthalic acid esters, phosphoric acid tris-alkyl esters and similar compounds may also be used in practicing the process of the present invention. Low molecular weight polyols (molecular weights in the range from 62 to 399) and relatively high molecular weight polyols (molecular weights in the range from 400 to around 10,000) are compounds known by those skilled in the art to be useful in the production of polyurethanes.

Where the aromatic uret dione diurea diamines of the present invention are used in the synthesis of polyurethanes, any of the starting components described above as suitable for the production of polyurethanes, such as relatively high molecular weight polyhydroxy or polyamino compounds, low molecular weight chain extenders, such as polyols or polyamines, and other polyisocyanates as well as standard auxiliaries and additives may be used. Suitable starting components are described in detail in German Offenlegungsschrift No. 2,854,384.

Aromatic uret dione diurea diamines in which the residue X is the 2,4'-disulfide radical and in which the diamine $H_2N—Y—NH_2$ has a molecular weight above 500 are excluded from the present invention. Compounds such as these are described in Applicants' German Patent Application No. P 31 35 542.0.

The diamines of the present invention may be filtered off from the solvents or plasticizers used during their production and recovered in the form of powders. The powders thus obtained may then be suspended in, for example, a relatively high molecular weight polyhydroxyl compound. The diamines of the present invention are, however, preferably produced directly in suspension in relatively high molecular weight polyhydroxyl compounds, preferably in substantially non-reactive polyhydroxyl compounds containing terminal secondary OH-groups (for example polypropylene ether polyols).

Having thus described our invention, the following Examples are given by way of illustration. All percentages given in these Examples are weight percents, unless otherwise indicated.

a slight pre-extension reaction (i.e. an oligomer-forming reaction in which two diisocyanates are joined by a diamine), a little excess aromatic diamine frequently remained dissolved in the liquid phase. That diamine was optionally washed out, filtered off under suction, dried and any agglomerates which had formed were size-reduced. The results are given in Table 1.

TABLE 1

Uret dione diurea diamines ("dimer diamines")

$$H_2N[-Y-N\overset{H}{\underset{}{|}}-\overset{O}{\underset{||}{C}}-\overset{H}{\underset{}{|}}N-X-N\diamond N-X-N\overset{H}{\underset{}{|}}-\overset{O}{\underset{||}{C}}-\overset{H}{\underset{}{|}}N]_n-Y-NH_2$$

(where the diamond represents the uret dione ring with two C=O groups)

| Example No. | Starting compounds aromatic diamines | Starting compounds uret dione diisocyanate | Reaction temp. [°C.] | Yield [% of theor.] | Molecular weight (MW) theor. | Molecular weight (MW) according to HClO₄—titr. | Degree of pre-extension "n" as calculated from the MW |
|---|---|---|---|---|---|---|---|
| 1 | 3,5-diethyl-2,4(35% 2,6)-diaminotoluene | dimeric-2,4-diisocyanato-toluene ("TT") | 20 | 78 | 704 | 901 | 1.37 |
| 2 | 3,5-diethyl-2,4(35% 2,6)-diaminotoluene | dimeric-2,4-diisocyanato-toluene ("TT") | 40 | 90 | " | 1273 | 2.08 |
| 3 | 3,5-diethyl-2,4(35% 2,6)-diaminotoluene | dimeric-2,4-diisocyanato-toluene ("TT") | 110 | 81 | " | 1061 | 1.68 |
| 4* | 3,5-diethyl-2,4(35% 2,6)-diaminotoluene | dimeric-2,4-diisocyanato-toluene ("TT") | 20 | 60 | ∞ | 1292 | 2.12 |
| 5 | 4,4'-diamino diphenyl methane | dimeric-2,4-diisocyanato-toluene ("TT") | 40 | 85 | 744 | 1198 | 1.83 |
| 6 | 2,4-diamino-toluene | dimeric-2,4-diisocyanato-toluene ("TT") | 40 | 95 | 592 | 980 | 1.83 |
| 7 | 3,5-diisopropyl-3',5'-diethyl-4,4'-diaminodiphenyl methane | dimeric-2,4-diisocyanato-toluene ("TT") | 40 | 75 | 1024 | 1471 | 1.65 |
| 8 | 3,5-diethyl-2,4-(35% 2,6)-diaminotoluene | dimeric 2,4'-diisocyanato-diphenyl sulfide | 40 | 98 | 892 | 1180 | 1.40 |
| 9 | 4,4'-diamino-diphenyl methane | dimeric 2,4'-diisocyanato-diphenyl sulfide | 40 | 98 | 932 | 1176 | 1.33 |
| 10 | 2,4-diamino-toluene | dimeric 2,4'-diisocyanato-diphenyl sulfide | 40 | 88 | 780 | 1000 | 1.33 |
| 11 | 3,5-diisopropyl-3',5'-diethyl-4,4'-diaminodiphenyl-methane | dimeric 2,4'-diisocyanato-diphenyl sulfide | 40 | 69 | 1212 | 1361 | 1.17 |
| 12 | 3,5-diethyl-2,4(35% 2,6)-diaminotoluene | dimeric 4,4'-diisocyanato-diphenyl methane | 20 | 80 | 856 | 980 | 1.39 |

*molar diamine: TT ratio = 1:1 (a very high molecular weight would be theoretically expected).

EXAMPLES

EXAMPLES 1-12

The uret dione diurea diamines of the present invention ("dimer diamines") were produced by dissolving or suspending the aromatic diamine in an NCO-inert solvent (such as toluene) and then adding portions of the total calculated quantity of dimeric diisocyanate (uret dione diisocyanate). The quantity of diamine and diisocyanate was such that the molar ratio was 2 moles of diamine to 1 mole of uret dione diisocyanate. A thick suspension soon formed and was stirred for 2 to 8 hours at 20° to 110° C. and preferably at 40° to 50° C. Due to

EXAMPLES 13-24

Mixtures of the uret dione diurea diamines of the present invention and polyester polyols were prepared as follows:

The quantity of uret dione diurea diamine indicated in Table 2 was stirred in the indicated quantity of polyester. This mixture was then stirred in a high-speed mixer until a fine suspension or paste was formed. Before use, the suspension or paste was degassed for 1 hour at 80° C. See Table 2 for the results of Examples 13 to 24.

TABLE 2

| Example No. | Example No. of uret dione di-urea diamine used | amine component (g) | polyester of adipic acid, ethylene glycol and 1,4-butane diol (1:1), MW 2000 (g) |
|---|---|---|---|
| 13 | 1 | 15 | 85 |
| 14 | 2 | 15 | 85 |
| 15 | 3 | 15 | 85 |
| 16 | 4 | 15 | 85 |
| 17 | 5 | 15 | 85 |
| 18 | 6 | 15 | 85 |
| 19 | 7 | 15 | 85 |
| 20 | 8 | 16.7 | 75 |
| 21 | 9 | 14.5 | 75 |
| 22 | 10 | 14.6 | 75 |
| 23 | 11 | 22.7 | 75 |
| 24 | 12 | 15.0 | 85 |

EXAMPLE 25

2000 g (1 mole) of a polyester of adipic acid and ethylene glycol were dehydrated for 1 hour at 100° C. 348 g (2 moles) of a mixture of 80% of 2,4-diisocyanatotoluene and 20% of 2,6-diisocyanatotoluene were added all at once and the mixture stirred at 80° C. until the theoretical final NCO-content of the prepolymer was 3.58%.

152.5 g of this NCO-prepolymer were degassed for 20 minutes at 110° C. 100 g of the paste produced in Example 15 were degassed for 1 hour at 80° C. Both components were mixed together and poured at 100° C. into a mold preheated to below 110° C. The mixture had a pouring time at 100° C. of 12 minutes and could be stored almost indefinitely at 40° C.

After the composition in the mold had been fully heated for 24 hours, a highly elastic material having the mechanical properties set out in Table 3 was obtained.

COMPARISON EXAMPLES 1-3

These Comparison Examples show that the advantageous mechanical properties of the elastomers crosslinked with the dimer diamines of the present invention are not achieved solely by extension and crosslinking with equimolar quantities of homogeneous amine crosslinkers or with polyol alone.

COMPARISON EXAMPLE 1

A homogeneously diamine-crosslinked comparison elastomer was prepared by using equal molar quantities of the parent aromatic diamine instead of a heterogeneous diamine within the scope of the present invention. 2.98 g of 3,5-diethyl-2,4-(35% 2,6)-diaminotoluene were dissolved in 89.2 g of a polyester of adipic acid, ethylene glycol/1,4-butane diol (1:1) having a molecular weight of 2000. 160 g of the NCO-prepolymer produced in Example 25 were then added.

COMPARISON EXAMPLE 2

To produce a non-diamine-crosslinked comparison elastomer, 170 g of the NCO-prepolymer obtained in Example 25 were reacted in the absence of a diamine chain extender solely with 142.4 g of the polyester of adipic acid and ethylene glycol/1,4-butane diol (molar ratio 1:1) used in Comparison Example 1 to form an elastomer.

Production of cast comparison elastomers from the same starting components by the conventional sequence of reaction steps was not possible due to the extremely short pot life of 0.5 minute or less at 80° C.

COMPARISON EXAMPLE 3

Dimeric tolylene diisocyanate and 3,5-diethyl-2,4(2,6)-tolylene diamine (65/35) were separately introduced at suitable points into the cast elastomer mixture. 7.42 g of dimeric tolylene diisocyanate were dissolved in 152.5 g of the NCO-prepolymer obtained in Example 25. 15 g of the diamine were dissolved in 85 g of polyester (adipic acid, ethylene glycol/1,4-butane diol (1:1) polyester molecular weight 2000). The NCO-prepolymer containing the dimeric tolylene diisocyanate in solution was then added at 80° C. The elastomer had to be processed extremely quickly on a laboratory scale to form an elastomer which appeared to have mechanical properties comparable to those of the elastomer of Example 25 with the exception that the pouring time at 80° C. was 15 minutes for the elastomer made with the diamines of the present invention rather than one or two minutes (as in comparison elastomers). However, a cast elastomer molding could not be produced because the polyaddition reaction was much too fast. Comparison of the properties of the elastomer produced in this example with those of the elastomer of Example 25 clearly shows the advantages of using heterogeneous crosslinking preadducts of uret dione diisocyanates and aromatic diamines over crosslinking with homogeneously dissolved reactants (in this case dimeric tolylene diisocyanate and diethyl tolylene diamine) for the production of high-grade polyurethane elastomers. See Table 3.

TABLE 3

Mechanical properties of the elastomer of Example 25 and the elastomers of Comparison Examples 1 and 2

|  | 25 | Comparison 1 | Comparison 2 |
|---|---|---|---|
| Pouring time at 80° C. [mins] | 15 | 2 | 8 |
| Mold-release time [mins] | 60 | 10 | 60 |
| Tensile strength [MPa] DIN 53 504 | 36.9 | 12.6 | 4.8 |
| Breaking elongation [%] DIN 53 504 | 606 | 805 | 256 |
| Tear propagation resistance DIN 53 515 [KN/m] | 22.7 | 17 | 15 |
| Shore Hardness A DIN 53 505 D | 78 / 26 | 77 / 25 | 68* / 18 |
| Elasticity [%] DIN 53 512 | 46 | 39 | 33 |
| Compression set after 24 h at 70° C. [%] DIN 53 517 | 13 | 64 | liquefaction at 70° C. |

*In this case, the Shore-A-hardness was based essentially on the crystallinity of the polyester as shown by the liquefaction which occurred during measurement of the compression set at 70° C.

EXAMPLE 26

As in Example 25, 100 g of the paste produced in Example 18 were added to 162 g of prepolymer of example 25.

COMPARISON EXAMPLE 4

As in Comparison Example 1, 83.9 g of polyester and 3.05 g of 2,4-diaminotoluene were added to 160 g of prepolymer of prepolymer of example 25.

TABLE 4

Mechanical properties of the elastomer of Example 26 and the elastomer of Comparison Example 4

|  | 26 | Comparison 4 |
|---|---|---|
| Pouring time at 80° C. [mins] | 10 | 2 |
| Mold release time [mins] | 60 | 12 |
| Tensile strength [MPa] DIN 53 504 | 30.8 | 17.9 |
| Breaking elongation [%] DIN 53 504 | 678 | 794 |
| Tear propagation resistance [KN/m] DIN 53 515 | 27.4 | 29.9 |
| Shore Hardness A DIN 53 505 D | 71 23 | 83 30 |
| Elasticity [%] DIN 53 512 | 47 | 35 |
| Compression set after 24 h at 70° C. [%] DIN 53 517 | 46 | 35 |

EXAMPLE 27

As in Example 25, 97.7 g of the paste prepared in example 23 were added to 135.3 g of prepolymer of example 25.

COMPARISON EXAMPLE 5

As in Comparison Example 1, 99.7 g of polyester and 5.81 g of 3,5-diisopropyl-3',5'-diethyl-4,4'-diaminodiphenyl methane were added to 160 g of prepolymer.

TABLE 5

Mechanical properties of the elastomer of Example 27 and the elastomer of Comparison Example 4

|  | 27 | Comparison 5 |
|---|---|---|
| Pouring time at 80° C. [mins] | 7 | 1.5 |
| Mold release time [mins] | 120 | 5 |
| Tensile strength [MPa] DIN 53 504 | 22.1 | 10.6 |
| Breaking elongation [%] DIN 53 504 | 620 | 794 |
| Tear propagation resistance [KN/m] DIN 53 515 | 20.3 | 18.4 |
| Shore hardness A DIN 53 505 D | 77 28 | 82 29 |
| Elasticity [%] DIN 53 512 | 48 | 42 |
| Compression set after 24 h at 70° C. [%] DIN 53 517 | 13 | 74 |

EXAMPLE 28

As in Example 25, 100 g of the paste prepared in example 24 were added to 143.2 g of prepolymer of example 25.

COMPARISON EXAMPLE

Identical with Comparison Example 1.

TABLE 6

Mechanical properties of the elastomer of Example 28 and the elastomer of Comparison Example 1

|  | 28 | Comparison 1 |
|---|---|---|
| Pouring time at 80° C. [mins] | 11 | 2 |
| Mold release time [mins] | 80 | 10 |
| Tensile strength [MPa] DIN 53 504 | 18.2 | 12.6 |
| Breaking elongation [%] DIN 53 504 | 708 | 805 |
| Tear propagation resistance [KN/m] DIN 53 515 | 17.7 | 17 |
| Shore hardness A DIN 53 505 D | 79 51 | 77 39 |
| Elasticity [%] DIN 53 512 | 27 | 25 |
| Compression set after 24 h at 70° C. [%] DIN 53 517 | 14 | 64 |

The following Examples illustrate use of the amines of the present invention in admixture with homogeneously soluble amine crosslinkers. These Examples show that the amines of the present invention can replace some of the homogeneous amine crosslinker in polyether polyurethanes to produce elastomers having distinctly improved properties.

EXAMPLE 29

The NCO-prepolymer was prepared as follows:

200 g (0.1 mole) of linear bifunctional polypropylene glycol (MW 2000) were dehydrated for 1 hour at 100° C. 34.8 g (0.2 mole) of 2,4-diisocyanatotoluene were added and the mixture stirred at 80° C. until the theoretical NCO-content of 3.58% was reached. 230.8 g of this prepolymer were degassed for 20 minutes at 110° C.

A mixture of 13.6 g of diethyl tolylene diamine and 13.44 g of the heterogeneous amine of Example 3 (dimeric tolylene diisocyanate and 2 moles of diethyl tolylene diamine) was added at 80° C. and the mixture poured into a mold preheated to 110° C. After heating for 24 hours at 110° C., an elastic material having the mechanical properties set out in Table 7 was obtained.

COMPARISON EXAMPLE 6

230.8 g of the same prepolymer as was used in Example 29 were degassed and crosslinked at 80° C. with 17.0 g of diethyl tolylene diamine. The mechanical properties of the resulting elastomer are set out in Table 7.

TABLE 7

Mechanical properties of the elastomer of Example 29 and the elastomer of Comparison Example 6

|  | 29 | Comparison 6 |
|---|---|---|
| Pouring time at 80° C. [mins] | 2 | 2 |
| Mold release time (110° C.) [mins] | 4 | 6 |
| Tensile strength [MPa] DIN 53 504 | 7.5 | 7.5 |
| Breaking elongation [%] DIN 53 504 | 750 | 950 |
| Tear propagation resistance [KN/m] DIN 53 515 | 25 | 21 |
| Shore hardness A DIN 53 505 D | 82 25 | 73 19 |
| Elasticity [%] DIN 53 512 | 56 | 54 |
| Compression set after 24 h at 70° C. [%] DIN 53 517 | 84 | 91 |

EXAMPLE 30

230.8 g of the same prepolymer as was used in Example 29 were degassed, followed by the addition at 80° C. (in the same way as described in Example 29) of a mixture of 17.44 g of molten 3,5-diamino-4-chlorobenzoic acid isopropyl ester and 13.44 g of the heterogeneous amine of Example 3. The properties of the resulting elastomer are given in Table 8.

COMPARISON EXAMPLE 7

21.8 g of 3,5-diamino-4-chlorobenzoic acid isopropyl ester were added at 80° C. to 230.8 g of the same prepolymer as was used in Examples 29 and 30. The mechanical properties of this elastomer are given in Table 8.

TABLE 8

Mechanical properties of the elastomer of Example 30 and the elastomer of Comparison Example 7

|  | 30 | Comparison 7 |
|---|---|---|
| Pouring time (110° C.) [mins] | 200 | 30 |
| Mold release time (110° C.) [mins] | 200 | 45 |
| Tensile strength [MPa] DIN 53 504 | 6 | 4.8 |
| Breaking elongation [%] DIN 53 504 | 485 | 420 |
| Tear propagation resistance [KN/m] DIN 53 515 | 25 | 19 |
| Shore hardness A DIN 53 505 D | 81 27 | 78 19 |
| Elasticity [%] DIN 53 512 | 45 | 42 |
| Compression set after 24 h at 70° C. [%] DIN 53 517 | 52 | 65 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. An aromatic uret dione diurea diamine corresponding to the formula

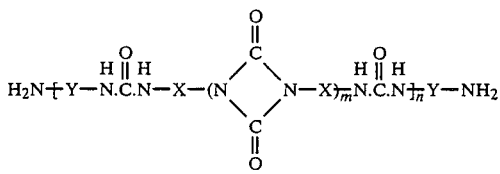

in which

X represents an aromatic radical having a molecular weight of from 76 to 499,

Y represents an aromatic radical having a molecular weight of from 76 to 10,000 or a radical derived from a high molecular weight diamine corresponding to the formula

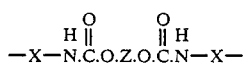

in which

Z represents a radical derived from a dihydroxy compound HO—Z—OH, provided that when Y represents a group derived from a diamine having a molecular weight ≧500 X does not represent a 2,4-diphenyl sulfide radical, m represents a number of from 1 to 10 and n represents a number of from 1 to 3.

2. The aromatic uret dione diurea diamine of claim 1 in which X represents a 2,4-tolylene and/or 4,4'-diphenyl methane and/or 2,4'-diphenyl methane radical.

3. The aromatic uret dione diurea diamine of claim 1 in which m represents a number of from 1 to 2.

4. The aromatic uret dione diurea diamine of claim 1 in which Y represents a 4,4'-diphenyl methane radical and/or 3,5-diisopropyl-3',5'-diethyl-4,4'-diphenyl methane radical and/or 3,5-diethyl-2,4-(2,6-) tolylene radical and/or 1,4-phenylene radical.

5. The aromatic uret dione diurea diamine of claim 1 in which Y represents a radical derived from a diamine having a molecular weight of from 1000 to 6000.

6. A process for the production of aromatic uret dione diurea diamines in finely particulate or suspended form which diamines correspond to the formula

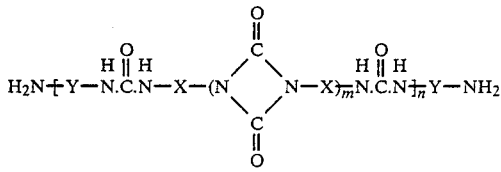

in which

X represents an aromatic radical having a molecular weight of from 76 to 499,

Y represents an aromatic radical having a molecular weight of from 76 to 10,000 or a radical corresponding to the formula

in which

Z represents a radical derived from a dihydroxy compound HO—Z—OH, provided that when Y represents a radical derived from a diamine H₂N—Y—NH₂ having a molecular weight ≧500, X does not represent a 2,4'-diphenyl sulfide radical, m represents a number of from 1 to 10 and n represents a number of from 1 to 3 comprising mixing an aromatic diamine H₂N—Y—NH₂ with a finely particulate diisocyanate corresponding to the formula

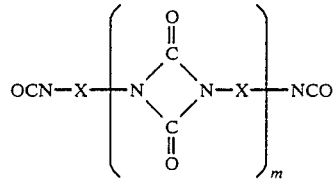

in a molar ratio of diamine to diisocyanate of at least 1.8:1.

7. The process of claim 6 in which the aromatic diamine H₂N—Y—NH₂ is used in the form of a solution in an isocyanate-inert solvent or in a relatively high molecular weight polyol.

8. The process of claim 6 in which the finely particulate uret dione diisocyanate is suspended in an isocyanate-inert solvent and/or relatively high molecular weight polyol.

9. A process for the production of urea-group-containing high molecular weight polyaddition products comprising reacting
(a) the aromatic uret dione diurea diamine of claim 1 with
(b) an NCO-prepolymer of polyol and excess polyisocyanate and/or a polyisocyanate at a temperature greater than 100° C. in quantities such that the equivalent ratio of NCO-groups to the sum of OH- and $NH_2$-groups is from 0.9 to 1.4.

10. The process of claim 9 in which a polyhydroxyl compound having a molecular weight of from 400 to 10,000 is included in the reaction mixture.

11. The process of claim 9 in which a chain extender having a molecular weight of from 32 to 399 is included in the reaction mixture.

12. The process of claim 9 further comprising the step of crosslinking the reaction product of (a) and (b) in the presence of excess OH- and/or $NH_2$-groups at a temperature above 140° C.

13. A self-crosslinking one component system at temperatures above 140° C. comprising the reaction product of a (i) long chain diamine $H_2N—Y—NH_2$ having a molecular weight of at least 500 where Y represents a radical corresponding to the formula

in which
Z represents a radical derived from a dihydroxy compound HO—Z—OH
with (ii) a uret dione diisocyanate.

* * * * *